US008087821B2

(12) United States Patent
Danley

(10) Patent No.: US 8,087,821 B2
(45) Date of Patent: Jan. 3, 2012

(54) INFRARED HEATED DIFFERENTIAL SCANNING CALORIMETER

(75) Inventor: Robert L. Danley, Collingswood, NJ (US)

(73) Assignee: Waters Technologies Corporation, Milford, MA (US)

(*) Notice: Subject to any disclaimer, the term of this patent is extended or adjusted under 35 U.S.C. 154(b) by 532 days.

(21) Appl. No.: 12/129,355

(22) Filed: May 29, 2008

(65) Prior Publication Data
US 2008/0304542 A1 Dec. 11, 2008

Related U.S. Application Data

(60) Provisional application No. 60/942,242, filed on Jun. 6, 2007, provisional application No. 60/942,245, filed on Jun. 6, 2007.

(51) Int. Cl.
G01N 25/00 (2006.01)
G01K 17/00 (2006.01)

(52) U.S. Cl. .................. 374/12; 374/31; 374/33
(58) Field of Classification Search ........... 374/12, 374/31, 33
See application file for complete search history.

(56) References Cited

U.S. PATENT DOCUMENTS

| 2,769,334 | A | 11/1956 | Soehngen |
| 3,491,581 | A | 1/1970 | Roberts et al. |
| 4,095,453 | A | 6/1978 | Woo |
| 4,117,050 | A | 9/1978 | Appel et al. |
| 4,429,684 | A | 2/1984 | Greiner |
| 4,850,713 | A | 7/1989 | Thery et al. |
| 5,363,391 | A | 11/1994 | Matthews et al. |
| 5,484,204 | A | 1/1996 | Danley |
| 5,509,733 | A | 4/1996 | Danley |
| 5,655,681 | A | 8/1997 | Vogel et al. |
| 6,403,925 | B1 | 6/2002 | Johnsgard et al. |
| 6,431,747 | B1 | 8/2002 | Danley |
| 6,488,406 | B2 | 12/2002 | Danley |
| 6,488,408 | B1 | 12/2002 | Laflamme et al. |
| 6,491,425 | B1 | 12/2002 | Hammiche et al. |
| 6,523,998 | B1 | 2/2003 | Danley et al. |
| 6,561,692 | B2 | 5/2003 | Danley |
| 6,578,367 | B1 | 6/2003 | Schaefer et al. |
| 6,648,504 | B2 | 11/2003 | Danley |
| 6,843,595 | B2 | 1/2005 | Danley |
| 7,025,497 | B2 | 4/2006 | Danley |
| 2002/0015801 | A1 | 2/2002 | Emch |
| 2003/0026319 | A1 | 2/2003 | Kinoshita |
| 2003/0101612 | A1 | 6/2003 | Granneman et al. |
| 2003/0142721 | A1 | 7/2003 | Hammer et al. |
| 2003/0165179 | A1 | 9/2003 | Danley |

(Continued)

OTHER PUBLICATIONS

International Search Report Dated Sep. 9, 2008.

(Continued)

Primary Examiner — Lisa Caputo
Assistant Examiner — Mirellys Jagan
(74) Attorney, Agent, or Firm — Timothy M. Bryan

(57) ABSTRACT

A heat flux differential scanning calorimeter (DSC) is disclosed. The DSC can be configured with a highly conductive sample assembly enclosure. The enclosure can include a high emissivity coating. In one embodiment, the enclosure extends along a longitudinal direction that is about the same as that of an infrared lamp assembly used to heat the enclosure, thereby increasing the efficiency of heating the sample enclosure. In one embodiment, a gas-filled thermal resistor is used to couple the measurement assembly to a heat sink, such that samples can be rapidly heated and rapidly cooled.

43 Claims, 8 Drawing Sheets

U.S. PATENT DOCUMENTS

2006/0140246 A1* 6/2006 Danley et al. ............... 374/14
2006/0187998 A1 8/2006 Danley

OTHER PUBLICATIONS

U.S. Appl. No. 12/130,553 filed on May 30, 2008.

United Kingdom Patent Application No. GB0919876.3, Examination Report, Mailing Date: Mar. 8, 2011, 7 pages.
United Kingdom Patent Application No. GB0919876.3, Examination Report, Mailing Date: Jun. 9, 2011, 2 pages.

* cited by examiner

INFRARED HEATED DIFFERENTIAL SCANNING CALORIMETER

This application claims the benefit of U.S. Provisional Application Nos. 60/942,242 filed Jun. 6, 2007 and 60/942,245 filed on Jun. 6, 2007, which are herein incorporated by reference in their entirety.

BACKGROUND

Field of the Invention

The present invention relates generally to apparatus and methods for measurements of the properties of materials, as those materials are heated or cooled.

Differential thermal analysis (DTA) and differential scanning calorimetry (DSC) can be performed at high sample heating rates, as described in U.S. Pat. No. 5,509,733 to Danley ("the '733 patent"), which discloses an "Infrared Heated Differential Thermal Analyzer" that allows both rapid heating and rapid cooling rates to be achieved. The '733 patent discloses the use of an infrared heat source to heat a differential thermal analysis (or potentially a differential scanning calorimetry) measuring assembly that is coupled to one or two heat sinks via one or two heat flow restricting elements that limit the rate of heat flowing between the heat sink and the measuring assembly. The heat sinks are cooled by either circulating a cold fluid through them or by supplying a sub-cooled liquid that evaporates within the heat sink carrying away heat. The sub-cooled liquid may be the refrigerant in a vapor compression refrigeration system or it may be an expendable coolant such as liquid nitrogen whose vapor is discharged to the atmosphere after cooling the heat sink.

In the '733 patent, the disclosed infrared furnace comprises a plurality of tubular quartz halogen lamps that radiate strongly in the near infrared portion of the electromagnetic spectrum and a reflector that encloses the lamps and the measuring assembly heated by the lamps. The reflector takes the form of a plurality of either elliptical or parabolic cylindrical surfaces equal to the number of lamps. The cylindrical surfaces are positioned relative to the lamps so that each lamp is at one of the foci of each ellipse or at the focus of each parabola. The lamps and the foci are equally spaced on a circle centered on the measuring assembly. The second focus of each elliptical cylinder of a multiple elliptical reflector is collinear with each of the other second foci and with the central axis of the measuring assembly. In this manner, a large fraction of the infrared radiation emitted by each lamp is directed by reflection from the elliptical surfaces toward the surface of the measuring assembly, thereby heating it. In the case of a multiple parabolic reflector, the foci of the parabolic surfaces are equally spaced on a circle centered on the measuring assembly with the axis of each parabola passing through the center of the measuring assembly. In this manner, a large fraction of the infrared radiation emitted by each lamp is reflected by the parabolic surface in parallel rays directed toward the measuring assembly, thereby heating the measuring assembly.

The heating assembly disclosed in the '733 patent can be used in conjunction with a measuring assembly that comprises a disk-type sensor constructed according to U.S. Pat. No. 4,095,453, where the sensor is joined to a pair of high thermal conductivity metal temperature-equalizing rings, one ring joined to each side of the sensor disk. The rings are joined to the heat restricting elements (also termed "thermal resistors" herein), which are in turn joined to the heat sinks. The heat restricting elements are thin-walled cylinders made of relatively low thermal conductivity metals that are resistant to high temperatures and to the large thermal stresses that may be imposed upon them. In the case of an apparatus having a single heat sink, the heat restricting element is joined to the temperature-equalizing ring located beneath the sensor and a second thin-walled section similar to the heat restricting element is joined to the upper temperature-equalizing ring. A removable cover is placed on the open end of the upper thin wall section to enclose the sample region. Its principal purpose is to prevent direct irradiation of the sensor and the sample pans by the lamps.

A major obstacle to using the apparatus, described in the '733 patent to perform differential scanning calorimetry is that the sensor and the sample pans exchange heat with the heat restricting elements and the heat sinks (and with the measuring assembly cover in the case of the thermal analyzer having a single heat sink). Given that the temperature differences between the sensor and the heat sinks and between the sensor and portions of the heat restricting elements is often of the order of several hundred degrees, and may even reach 1000° C. or more, the heat exchange may be quite large. Since this heat does not flow through the sensor, it is not measured; thus it constitutes a heat flow rate measurement error. For experiments where quantitative heat flow rate measurement is not necessary, such as experiments during which only the temperature of a transition is measured, and only knowledge of the direction of the heat exchange, i.e. whether the transition is exothermic or endothermic, is required, the apparatus of the '733 patent may be adequate.

In addition, although the apparatus disclosed in the '733 patent has a rapid thermal response based on the low mass of the measuring assembly, the apparatus is not configured to maximize the efficiency of the radiant heat exchange between the lamps and the measuring assembly. Given that the sensor is heated essentially by irradiation of the heat restricting elements and the thin-walled enclosure above the sensor in the case of the single heat sink configuration, or by radiation of both heat restricting elements in the case of the dual heat sink configuration, the area that intercepts radiation thereby heating the measuring assembly is a small fraction of the total irradiated surface area. Moreover, despite the fact that the heat sinks are coated with a highly infrared reflective coating such as gold, the heat sinks and the reflector nevertheless absorb some of the energy emitted by the lamps because the coating is not perfectly reflective. At each reflection, a small portion of the radiation is absorbed and thus is no longer available to heat the measuring assembly. Because the area to be heated is very small in comparison to the combined reflector and heat sink area, very nearly all of the radiation emitted by the lamps is absorbed by the reflector and heat sink, rather than by the measuring assembly.

A further limitation of the apparatus disclosed in the '733 patent is the presence of a quartz glass tube that encloses the measuring assembly. The quartz glass tube allows an enclosed space to be purged with a gas that can serve as a protective environment for the sample when an inert purge gas is used, or can provide a reactive environment when a reactive purge gas is used. Although the quartz glass is highly transparent to near infrared radiation, it nevertheless absorbs a small fraction of the near infrared radiation and strongly absorbs infrared radiation having a wavelength greater than about 4 µm. Thus, absorption of radiation by the quartz tube further reduces the efficiency of radiant heating of the measuring assembly. It will therefore be appreciated that the efficiency of the infrared heating system disclosed in the '733 patent is relatively low and only a small fraction of the energy supplied to the lamps actually heats the measuring assembly.

In addition, apparatus like that disclosed in the '733 patent require cooling because the reflector absorbs most of the radiation emitted by the lamps. The '733 patent teaches cooling the reflector by circulating a coolant (e.g., water) through coolant passages in the reflector assembly or by the use of cooling fins on the exterior of the reflector. The air circulation is either forced through the use of a fan or by natural convection, relying on the buoyancy of air heated by the fins. When the minimum operating temperature of the heat sinks is below the minimum temperature of the reflector (for example, when the heat sink is cooled using a low temperature coolant like liquid nitrogen and the reflector is cooled by water), the measuring assembly is surrounded by a reflector that is substantially warmer than the measuring assembly, resulting in heating of the measuring assembly by the reflector. Cooling rates of the measuring assembly are thereby reduced and the minimum temperature the measuring assembly can reach is increased. Thus, the method of cooling the reflector limits the performance of the apparatus of the '733 patent.

On the other hand, a conventional heat flux DSC can be constructed by installing a sensor within a uniform temperature enclosure that is heated and cooled according to the desired experimental temperature program. This greatly reduces the temperature differences between the sensor and sample pans and their surroundings, thereby reducing the unmeasured heat exchange between sensor and sample pans and the enclosure. However, such enclosures generally have relatively high heat capacities and thus are not well suited to heating and cooling at high rates. Moreover, the enclosures are typically heated by resistance heating elements that must be electrically and thermally insulated from the DSC enclosure. Thus, the heating elements do not transfer heat rapidly to the DSC enclosure and when power is removed they cool slowly. The heating elements, electrical and thermal insulation of the heating elements also add mass to the DSC, increasing its heat capacity, further limiting the ability to heat and cool rapidly.

BRIEF SUMMARY OF THE INVENTION

In one configuration of the present invention, a differential scanning calorimeter comprises a measurement assembly having a differential scanning calorimeter sensor assembly for receiving a sample that is installed in a cavity within an elongated cylinder, and an infrared lamp assembly disposed circumferentially around the elongated cylinder having a length substantially similar to that of the cylinder. The infrared lamp assembly preferably comprises a plurality of tubular lamps each having a longitudinal axis arranged parallel to the axis of the elongated cylinder, and an infrared reflector comprising a plurality of partial cylindrical surfaces that each describe a cylindrical shape that has a focus collinear with the axis of each tubular lamp. The calorimeter further comprises a thermal resistor coupled to the measurement assembly, wherein the thermal resistor is disposed substantially outside of a region whose perimeter is defined by a cavity within the lamp assembly, and a heat sink thermally coupled to the thermal resistor and to the infrared reflector.

In another configuration of the present invention, a differential scanning calorimeter comprises a measurement assembly including a differential scanning calorimeter sensing assembly for receiving a sample. The measurement assembly comprises an elongated high thermal conductivity cylinder having a cavity in which the DSC sensing assembly is situated and a high emissivity outer surface. The calorimeter further comprises an infrared lamp assembly disposed circumferentially around the elongated cylinder and having a length substantially similar to that of the elongated cylinder. The infrared lamp assembly comprises a plurality of tubular lamps arranged with their longitudinal axis parallel to the axis of the elongated cylinder, and an infrared reflector comprising a plurality of partial cylindrical surfaces that each describe a cylindrical shape that has a focus collinear with the axis of each tubular lamp. The calorimeter also includes a thermal resistor thermally coupled to the measurement assembly and a heat sink thermally coupled to the thermal resistor and to the infrared reflector.

In yet another configuration of the present invention, a differential scanning calorimeter comprises a measurement assembly including a differential scanning calorimeter sensing assembly for receiving a sample, where the measurement assembly comprises an elongated cylinder. The calorimeter also includes an infrared lamp assembly disposed circumferentially around the elongated cylinder and having a length substantially similar to that of the elongated cylinder, where the infrared lamp assembly comprises a plurality of tubular lamps each having a longitudinal axis parallel to an axis of the elongated cylinder, and an infrared reflector comprising a plurality of partial cylindrical surfaces that each describe a cylindrical shape that has a focus collinear with the axis of each tubular lamp. The calorimeter further includes a thermal resistor coupled to the measurement assembly and having a configurable thermal resistance, and a heat sink thermally coupled to the thermal resistance and to the infrared reflector, wherein the thermal resistor is operable to vary the thermal resistance between the measurement assembly and the heat sink during sample measurement.

DETAILED DESCRIPTION OF EMBODIMENTS

Figure 1:
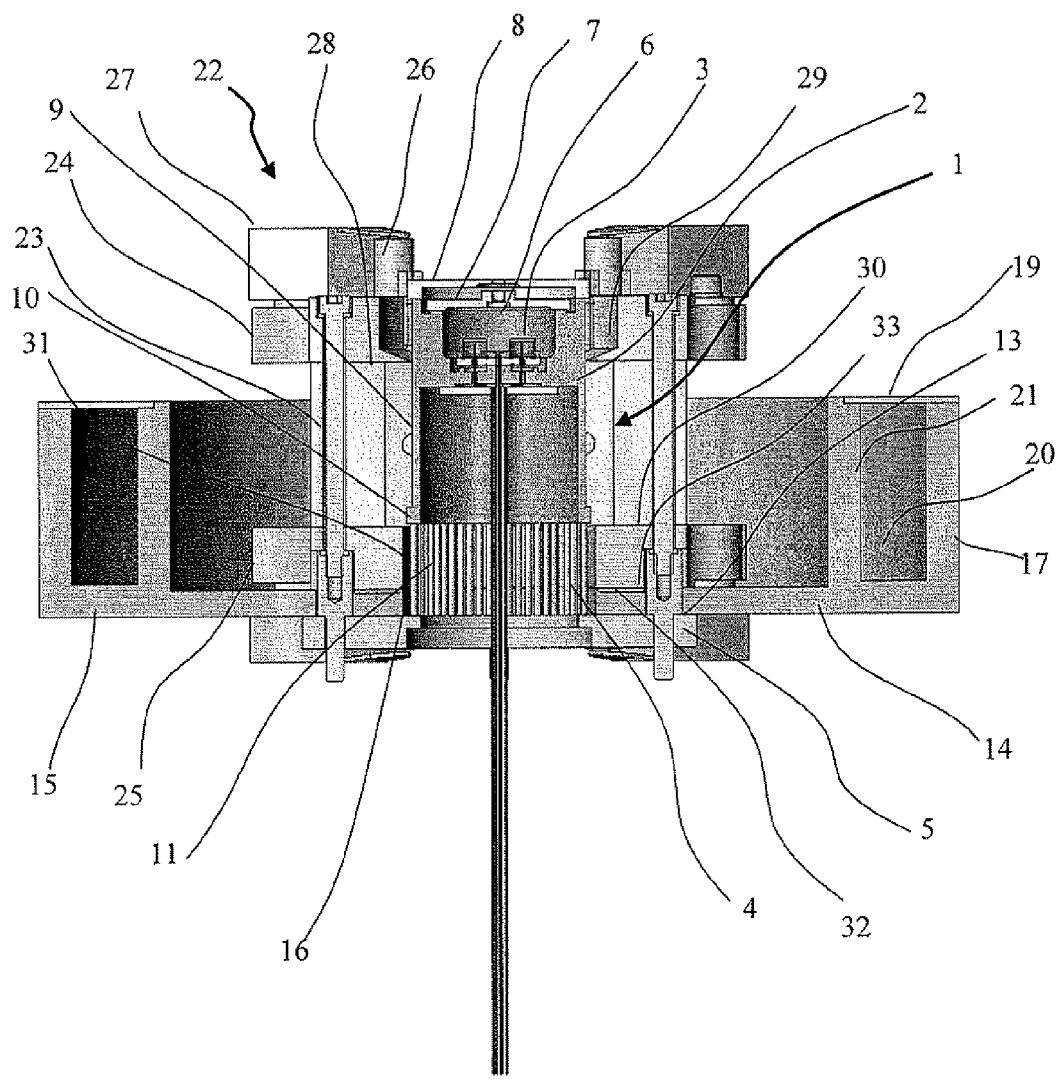
FIG. 1 is a schematic diagram that shows a vertical cross-section through the centerline of a calorimeter measuring assembly according to one configuration of the present invention.

In order to clarify the present invention, embodiments of the present invention are discussed below with respect to FIGS. 1-4.

In one configuration of the present invention, a heat flux differential scanning calorimeter comprises an infrared furnace used to heat a measuring assembly that incorporates a high thermal conductivity enclosure similar to that of a conventional DSC. The enclosure reduces temperature difference errors that result from heat exchange between the sensor, sample pans and their surroundings. Given that such an enclosure is considerably more massive than that described, for example, in the '733 patent, much more infrared energy from the lamps must be delivered to the measuring assembly to achieve a desired heating rate, and more energy must be removed to achieve a desired cooling rate. In configurations of the present invention described in detail below, the exterior surface of a DSC enclosure that surrounds a measurement assembly is an elongated circular cylinder that is approximately equal in length to a reflector cavity and lamp assembly that form an infrared heating assembly. In this manner, the DSC enclosure intercepts a greater fraction of the energy emitted by the lamps and reflected by the reflector.

Preferably, the DSC enclosure comprises a high emissivity exterior surface. In one configuration of the present invention, the DSC enclosure comprises a single high emissivity material. In another configuration, the DSC enclosure comprises an enclosure, such as a cylindrical enclosure whose emissivity is not high in an inner portion of the cylinder walls, but whose exterior surface is coated or laminated with a high emissivity layer to greatly increase the absorption of radiation arriving at the surface. In addition, in embodiments of the present invention, the measuring assembly is constructed without a surrounding quartz tube which is conventionally used to enclose the measuring assembly, such as that depicted in the '733 patent. This further improves heat exchange efficiency and also allows the lamps to be positioned closer to the measuring assembly, which, in turn allows the reflector surface area to be reduced. The ratio of heated area to reflector area is thus increased, further improving the efficiency of infrared heating.

Preferably, a single heat sink is employed in the DSC apparatus, and is located externally to the infrared furnace reflector, so that the heat sink is not directly heated by radiation, still further improving efficiency of infrared heating. The heat sink may be cooled by circulating water or some other fluid as a coolant. Alternatively, the heat sink may be cooled by evaporation of a sub-cooled liquid, which may be the refrigerant in a vapor compression refrigeration system, or an expendable coolant such as liquid nitrogen whose vapor is discharged to the atmosphere.

In one configuration of the present invention, the heat flux DSC includes a single thermal resistor used to thermally connect the measuring assembly to the external heat sink located externally to the reflector. Preferably, the thermal resistor is also located externally to the reflector, wherein the resistor is disposed outside the region defined by the reflector cavity. The thermal resistor may be comprised of a solid material having the requisite composition and geometry to create the desired heat flow restriction, or it may be a small gap filled with gas such that the gas thermal conductivity and the gap dimension create the desired heat flow restriction. When the thermal resistor comprises a gas-filled gap, the gas composition may be changed to modify the magnitude of its thermal resistance. Rather than using a separate cooling system for the reflector as described in the prior art, in configurations of the present invention the reflector is also coupled to the heat sink so that it too is cooled by the heat sink. In this manner, the cooling rates and the minimum temperature achieved by the apparatus are improved. In addition, the device is simplified by elimination of a separate cooling system for the infrared reflector.

FIG. 1 shows a vertical cross-section through the centerline of a calorimeter measuring assembly according to a configuration of the present invention in which a solid thermal resistor is used to couple the measuring assembly to the heat sink. The measuring assembly 1 comprises high thermal conductivity enclosure 2, sensor assembly 3, thermal resistor 4 and cooling flange 5. In one embodiment of the present invention, high thermal conductivity enclosure 2 is made of commercially pure silver in the shape of a cylinder, preferably a cylinder having an approximately circular cross-section ("circular cylinder"), and includes cavity 6, which is closed by inner lid 7 and outer lid 8 that are both also made of silver. Cylindrical outer surface 9 is coated with a high emissivity coating that enhances the infrared absorptivity of the surface, where high emissivity is defined as normal total emissivity greater than about 0.9. One such suitable coating is Laser Black, a proprietary coating produced by Epner Technology Inc. of Brooklyn, N.Y. In one configuration of the present invention, heat flux differential scanning calorimeter sensor assembly 3 as described in U.S. Pat. No. 6,431,747 and in U.S. patent application Ser. No. 11/843,225, filed Aug. 22, 2207 (which is based on U.S. Patent Application No. 60/839,673, filed Aug. 24, 2006.) (each of which are incorporated herein by reference in their entirety), is inseparably joined to the base of cavity 6 of enclosure 2 by brazing, which ensures that the heat exchange between the sensor and the enclosure is highly repeatable.

A flange 10 at the lower end of enclosure 2 provides a means for the enclosure to be joined to thermal resistor 4, which comprises a plurality of slender rods 11. Preferably, slender rods 11 are inseparably joined to cooling flange 5, for example, by brazing. The material and structure of slender rods 11 are chosen to withstand mechanical stresses that develop during expansion and contraction of enclosure 2 relative to cooling flange 5. For example, rods 11 may be fabricated from nickel Cooling flange 5 provides a flat mounting surface 13 to which the heat sink, or heat exchanger 14 is attached. In one configuration of the present invention, enclosure 2, sensor assembly 3 and cooling flange 5 are the same as their corresponding elements described in U.S. Pat. No. 6,523,998 ("the '998 patent) to Danley et al., which is incorporated by reference herein in its entirety. Notably, however, the apparatus of the '998 patent employs resistive heating elements and associated structures to heat a sample, as opposed to an infrared furnace assembly 22 (see FIG. 1) that is employed in configurations of the present invention and described below.

Heat exchanger 14 includes a flange 15 having a flat mounting surface 16 that contacts flat mounting surface 13 of cooling flange 5. Body 17 of the heat exchanger is integral with flange 15 and includes a bottom, inner and outer walls joined to cover 19 to form cavity 20 that contains the coolant which exchanges heat with the internal surface 21 of the body. Fins may be added to increase the area of lateral surface 21 if needed according to the magnitude of heat exchange. If the coolant is liquid nitrogen, the flow rate of liquid nitrogen may be controlled using the apparatus and the method disclosed in U.S. Pat. No. 6,578,367 to Schaefer, et al, which is incorporated by reference herein in its entirety. Alternatively, the flow rate of liquid nitrogen may be controlled using the apparatus and the method disclosed in U.S. provisional patent application No. 61/015,731, to Danley, filed Dec. 21, 2007, which is incorporated by reference herein in its entirety and attached herewith as Appendix A.

In the configuration of the present invention depicted in FIG. 1, infrared furnace assembly 22 comprises reflector body 23, top plate 24, bottom plate 25, four lamps 26 and eight lamp holders 27. Reflector body 23 contains a cavity comprising four intersecting parallel vertically oriented portions of partial quadric cylinders, for example, partial elliptical cylinders, in which a tubular quartz halogen lamp 26 is situated at one focus of each of a set of four quadric cylinders that are defined by the partial quadric cylinder portions that form the cavity walls. In the configuration shown in FIG. 1, the quadric cylinders are elliptical cylinders in which a second focus of each of the elliptical cylinders is collinear and located at the center of the reflector body collinear with the central axis of the measuring assembly. The lamps may be, for example, 250 watt T-3 configuration lamps with an RSC (recessed single contact) base and 1¼" lighted filament length, thus delivering 1000 watts total power. The cavity of the reflector is polished and has a high infrared reflectivity coating applied to it. High infrared reflectivity is defined as having a hemispherical total reflectivity of at least 0.95 in the near infrared electromagnetic spectrum up to 12 μm wavelength. One such suitable coating is Laser Gold, a proprietary coating produced by Epner Technology Inc. of Brooklyn, N.Y. Reflector top plate 24 is flat and has mounting lugs (not shown) for four lamp holders 27 that hold and make electrical contact with the upper end of each lamp. The surface 28 of the plate facing the cavity of the reflector block is polished and has a high infrared reflectivity coating applied to it. A hole 29 that extends through the plate allows access to the measuring assembly for loading and unloading samples. Reflector bottom plate 25 is flat and has mounting lugs (not shown) for the four lamp holders 27 that hold and make electrical contact with the lower end of each lamp. Surface 30 of the plate facing the cavity of the reflector block is polished and has a high infrared reflectivity coating applied to it. A hole 31 that extends through the plate allows the thermal resistor to pass through the plate. Outer flat surface 32 of the bottom plate mates with flat surface 33 of flange 15 of the cooler, thus cooling the entire reflector assembly.

Figure 2:
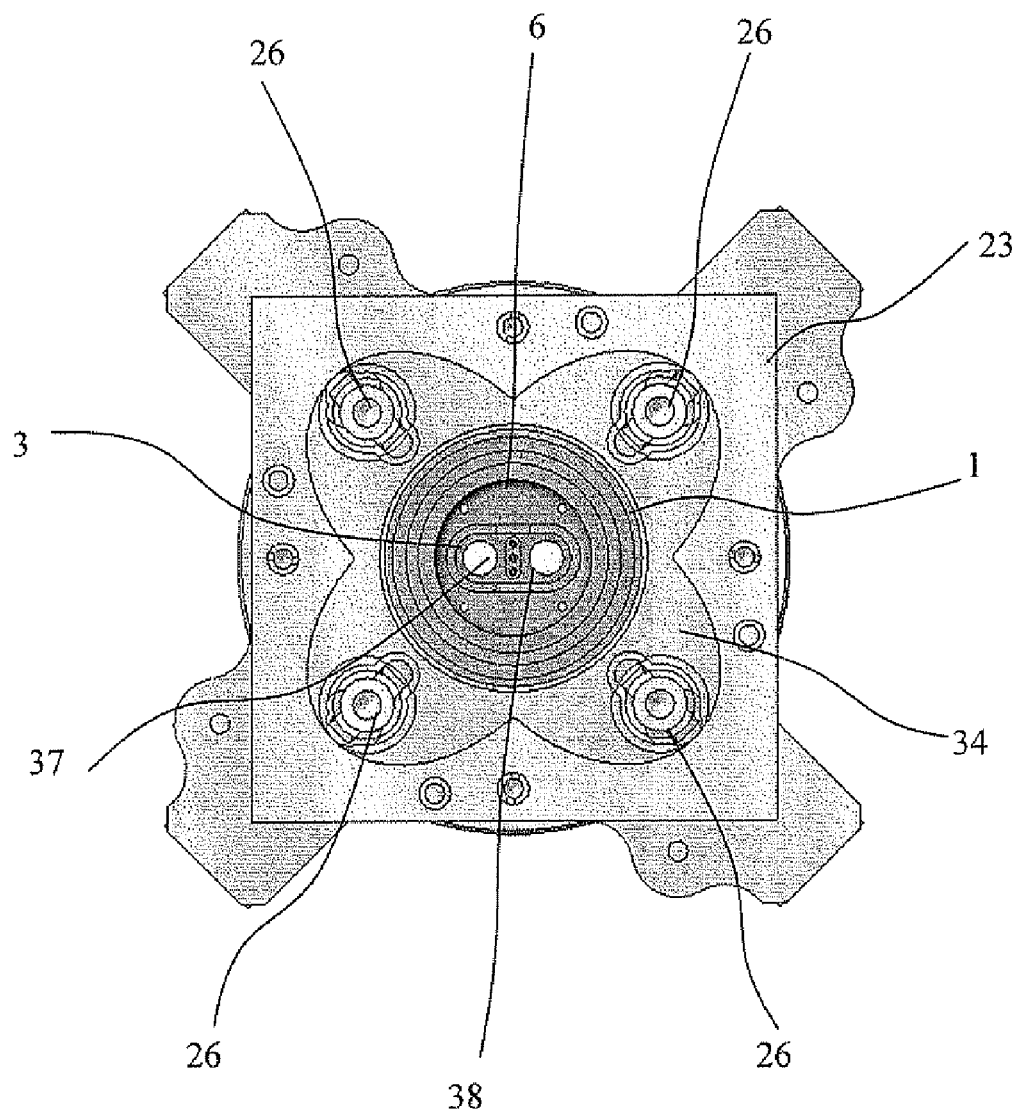
FIG. 2 shows a horizontal cross-sectional view through the infrared furnace and measuring assemblies depicted in FIG. 1.

FIG. 2 shows a horizontal cross-sectional view through the infrared furnace and measuring assemblies. Cavity 34 of reflector body 23 comprises four intersecting parallel partial elliptical cylinders arranged such that one focus of each partial elliptical cylinder is located equally spaced on a circle centered on the measuring assembly 1. Referring again to FIG. 1, the cavity 34 of the reflector block is designed to be approximately the same length as (for the purposes of this disclosure, use of the phrases "approximately the same length" or "approximately equal" means the ratio of the length of reflector block cavity 34 and enclosure 2 along its axis is about 0.8 to 1.2, preferably 0.9 to 1.1) and aligned with conductive enclosure 2, such that enclosure 2 is surrounded by the reflector block cavity 34 over its entire length. In order to heat enclosure 2 efficiently, reflector block cavity 34 is designed not to extend substantially beyond the length of enclosure 2.

A lamp 26 is located at each of the four equally spaced foci. The second focus of each ellipse is collinear with each of the other second foci and with the centerline of the measuring assembly 1. Sensor assembly 3 is located symmetrically with respect to the centerline of the measuring assembly within cavity 6 of enclosure 2 (shown in FIG. 2) and has a sample position 37 and a reference position 38 on which sample containers and reference containers are placed. During experiments, the sample container contains a sample; while the reference container may be empty or may contain a reference material.

It should also be noted that the embodiments of the present invention disclosed above with respect to FIGS. 1-2 may be used to practice the inventions disclosed in U.S. Pat. Nos. 6,488,408; 6,561,692; 6,648,504; and 6,843,595.

Figure 3:
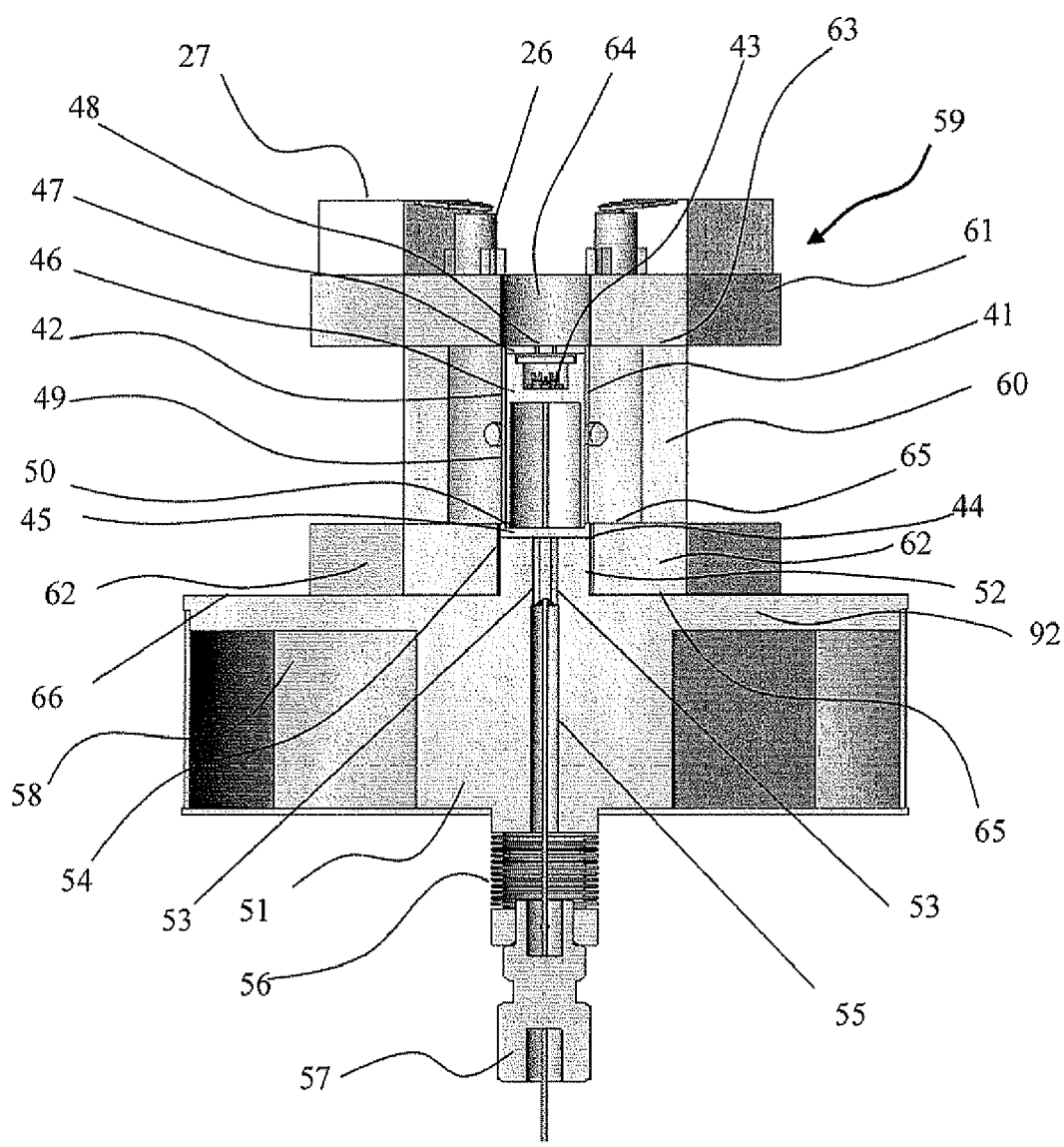
FIG. 3 is a schematic diagram that shows a vertical cross-section through the centerline of a calorimeter measuring assembly according to another configuration of the present invention.

FIG. 3 shows a vertical cross-section through the centerline of the calorimeter measuring assembly for a configuration of the present invention that uses a gas-filled gap thermal resistor to couple the measuring assembly to the heat silk. To further enhance the heating and cooling rates attainable, the measuring assembly is greatly reduced in size, as are those of the sample and sample containers employed. Measuring assembly 41 comprises high thermal conductivity enclosure 42, sensor assembly 43 and thermal resistor 44. In one embodiment of the present invention, high thermal conductivity enclosure 42 is made of commercially pure silver, and is arranged in the shape of a cylinder, preferably a cylinder having circular cross-section ("circular cylinder"), that includes cavity 46, which is closed by inner lid 47 and outer lid 48 that are both also made of silver. Cylindrical outer surface 49 is coated with a high emissivity coating that enhances the infrared absorptivity of the surface. One such suitable coating is LaserBlack, a proprietary coating produced by Epner Technology Inc. of Brooklyn, N.Y.

In one configuration of the present invention, heat flux differential scanning calorimeter sensor assembly 43 as described in U.S. Pat. No. 6,431,747 and in patent disclosure (U.S. Patent Application No. 60/839,673), is inseparably joined to the base of cavity 46 of enclosure 42 by brazing, which ensures that the heat exchange between the sensor and the enclosure is highly repeatable. Because the sample and sample container sizes in this embodiment are very small, the sensor assembly 43 is preferably fitted with cylindrical cavities on both the sample and reference positions to aid in placing and holding the sample containers, (that is, containers that hold materials placed in either sample or reference positions). This arrangement contrasts with that of sensor assembly 3 of the previous embodiment, which includes flat platforms to support the sample containers. Further, the cylindrical cavities reduce the contact resistance between the sample capsules and the sensor by increasing the surface area for heat exchange. This aids in reducing the temperature difference between sample capsule and sensor when high heating and cooling rates are employed.

The top of gas-filled gap thermal resistor 44 comprises a flat silver plate 50 that is an integral part of the measuring assembly. The opposite surface of the thermal resistor 44 is formed by heat sink extension 52 of heat sink 51 that extends upwards into the reflector bottom plate to support the measuring assembly.

In accordance with one embodiment of the present invention, gas-filled gap 45 is a simple gap that results when two nominally flat surfaces are pressed together. For example, heat sink 51, which comprises outer portion 92 and heat sink extension 52 disposed in the center of heat sink 51, can be configured such that heat sink extension 52 comes into nominal contact with plate 50 when heat sink 51 is assembled to measurement assembly 41. In such a configuration, the resulting gas-filled gap occurs because the two nominally flat surfaces—plate 50 and the top of heat sink extension 52—are not perfectly flat, so that gas fills spaces between the nominally flat surfaces. The average vertical dimension of the resulting gas-filled gap corresponds to the average vertical separation between the top of heat sink extension 52 and the bottom of plate 50 taken over the planar area between heat sink extension 52 and plate 50. Thus, because neither the surface of heat sink extension 52 or that of plate 50 may be ideally flat, that is, each surface has some degree of roughness or non-planarity, when plate 50 and heat sink extension 52 are brought into contact, there may be many gaps between the actual points of contact between plate 50 and heat sink extension 52, which can be expressed as an average vertical gap.

In another embodiment of the present invention, as depicted in FIG. 3, the heat sink extension 52 can be configured such that a finite vertical gap 45 exists between plate 50 and the top of heat sink extension 52 (that is, there is no contact between plate 50 and heat sink extension 52), when surface 66 is assembled against bottom plate 62.

Exemplary dimensions of gas-filled gap 45 include a lateral width (diameter) ranging from a few millimeters to several centimeters, corresponding to the diameter of heat sink extension 52, and a vertical dimension ranging from a few tenths of a millimeter down to nominally zero millimeters, as discussed above. However the present invention is not limited to any particular size range of gas-filled gap 45, nor is the invention limited to a particular vertical-to-horizontal ratio of gas-filled gap 45. Two small diameter passages 53 that extend through the heat sink extension supply gas to thermal resistor 44; passages 53 are supplied by a larger passage 55 that passes through the heat sink where it is closed by a bellows 56 and a seal arrangement 57 to which the gas source is connected. In accordance with another embodiment of the present invention, bellows 56 also performs the additional function of holding the measuring assembly in place and maintaining the dimensions of gap 45 of the thermal resistor. When the measuring assembly is installed to heat sink 51, it is held in place against heat sink extension 52 and the bellows 56 is compressed. Seal arrangement 57 is configured to be tightened, clamping the seal arrangement to the thermocouple protection tubes and thereby exerting a force that holds plate 50 of the measuring assembly firmly in place against the heat sink extension 52. Tightening of seal arrangement 57 tends to pull plate 50, which is coupled to thermocouple protection tubes that pass through passage 55, towards heat sink extension 52. Accordingly, the tightening process can be used to maintain plate 50 in contact with heat sink extension 52.

In another embodiment of the present invention, thin spacers (not shown) are disposed within gas-filled gap 45 to increase the effective thermal resistance. In one embodiment of the present invention, the spacers are thin metal sheets that extend horizontally across the diameter of gas-filled gap 45. For example, the thin metal sheets can have be circular disks having a diameter that ranges in size up to that of gas-filled gap 45. Thus, the thin spacers are disposed in a layer-like fashion within gas-filled gap 45.

In accordance with embodiments of the present invention, even though thin sheets of metal typically have inherently low thermal resistance because they are thin and are made of relatively high thermal conductivity material, the thermal resistance of gas-filled gap 45 is increased when the thin sheets are horizontally disposed within the gap. This is because the presence of one or more horizontal thin metal sheets increases the thermal resistance by increasing the number of thin gas layers within the interface between plate 50 and extension 52. Without any thin horizontal metal sheet spacer ("spacer") within gas-filled gap 45, there is only a single gas layer between plate 50 and extension 52. Addition of one spacer increases the number of gas layers to two: one gas layer between the spacer and plate 50, and one gas layer between the spacer and extension 52. Because the top and bottom surfaces of each spacer retain a degree of non-planarity or roughness, many gaps persist between adjacent spacers even when they are brought into contact with each other, producing an effective gas layer between adjacent spacers. Accordingly, insertion of each additional spacer within gap 45 increases by one the number of gas layers, thereby increasing the thermal resistance of the gap assembly for any given gas composition. In one embodiment of the present invention, two spacers are disposed within gap 45, providing three gas layers within the gap.

Exemplary spacer thickness can be about 0.0005" to about 0.01," which thickness range is suitable to produce small gas-filled gaps 45 as described below.

In accordance with an embodiment of the present invention, one or more thin spacers are placed horizontally in a spacer stack (that is, the spacers are arranged in layer-like fashion) between heat sink extension 52 and plate 50, after which seal arrangement 57 is tightened such that the spacer stack comes into nominal contact with both heat sink extension 52 and plate 50. In one embodiment of the present invention, the total average vertical gap spacing, which is the sum of the average vertical gaps created between any spacers in the stack, the average gap between the top of the spacer stack and plate 50, and the average gap between the bottom of the spacer stack and heat sink extension 52, is about 0.0001"- 0.002." By selecting the appropriate number of spacers, together with the appropriate surface roughness, among other parameters, the total average vertical gap can be engineered to a achieve a desired dimension, to provide for a desired range of achievable thermal resistance.

The user of thin spacers provides multiple advantages for engineering thermal resistance in assembly 59. For example, if a user desires a range of thermal resistance that requires an average vertical gap to be about 0.001," in order to try to achieve the vertical separation the top of extension 52 could be brought into approximately 0.001" proximity to plate 50. However, it can be exceedingly difficult to reproducibly achieve such a small gap, for example, by adjusting seal arrangement 57, let alone to determine when the appropriate gap is achieved. In contrast, the use of thin spacers facilitates more accurate control of a vertical gap by allowing a user to assemble heat sink extension 52 and plate 50 together until contact is made on both top and bottom surfaces of the interposed thin spacer stack, at which point a tight fit is achieved in which each spacer is in contact with an external surface on the top side and bottom side. Because the surface roughness of the top of heat sink extension 52 and bottom of plate 50, as well as that of the interposed spacers, tends to persist, substantially the same effective gap can be produced each time heat sink extension 52 is tightened against plate 50. In this manner, a user could determine by trial the number of spacers needed to produce the desired gap dimension or the desired thermal resistance range.

Moreover, by choosing the composition of the gas supplied to gap 45, the thermal resistance and hence the rate of heat flow between the measuring assembly and the heat sink can be tailored to produce the desired heating and cooling rates. For example, when a low thermal conductivity gas like argon is supplied to the gap, higher heating rates and lower cooling rates may be achieved. When a high thermal conductivity gas like helium is supplied to the gap, lower heating rates and higher cooling rates may be achieved. Coolant is supplied to cavity 58 in the heat sink where the coolant contacts surfaces of the heat sink to extract heat. Fins may be added to increase the area of the heat sink surface if needed according to the magnitude of heat exchange. If the coolant is liquid nitrogen, the flow rate of liquid nitrogen may be controlled using the apparatus and the method disclosed in U.S. Pat. No. 6,578, 367 to Schaefer, et al, or by the apparatus described in Appendix A.

Infrared furnace assembly 59 comprises reflector body 60, top plate 61, bottom plate 62, four lamps 26 and eight lamp holders 27 (one lamp holder 27 located on the top and one lamp holder 27 located on the bottom of each lamp 26). Reflector body 60 contains a cavity comprising four parallel vertically oriented intersecting elliptical cylinders in which a lamp is situated at one focus of each of the four elliptical cylinders. The other foci of the elliptical cylinders are collinear and located at the center of the reflector body collinear with the central axis of the measuring assembly. The lamps may be 250 watt lamps having a T-3 configuration with an RSC (recessed single contact) base and 1¼" lighted filament length, thus delivering 1000 watts total power. The cavity of the reflector is polished and includes a coating that has very high infrared reflectivity, which is defined as having a hemispherical total reflectivity of at least about 0.95 in the near infrared electromagnetic spectrum up to 12 µm wavelength. One such suitable coating is Laser Gold, a proprietary coating produced by Epner Technology Inc. of Brooklyn, N.Y. Reflector top plate 61 is flat and has mounting lugs (not shown) for four lamp holders 27 that hold and make electrical contact with the upper end of each lamp. Surface 63 of the plate facing the cavity of the reflector block is polished and has a coating applied that has very high infrared reflectivity. A hole 64 that extends through the plate allows access to the measuring assembly for loading and unloading samples. Reflector bottom plate 62 is flat and has mounting lugs for four lamp holders that hold and make electrical contact with the lower end of each lamp. Surface 65 of the plate facing the cavity of the reflector block is polished and has a coating applied that has very high infrared reflectivity. A hole 54 that extends through the plate allows heat sink extension 52 and thermal resistor 44 to enter the bottom plate and support the measuring assembly. Outer flat surface 85 of the bottom plate mates with flat surface 66 of the heat sink thus cooling the entire reflector assembly.

Figure 4:
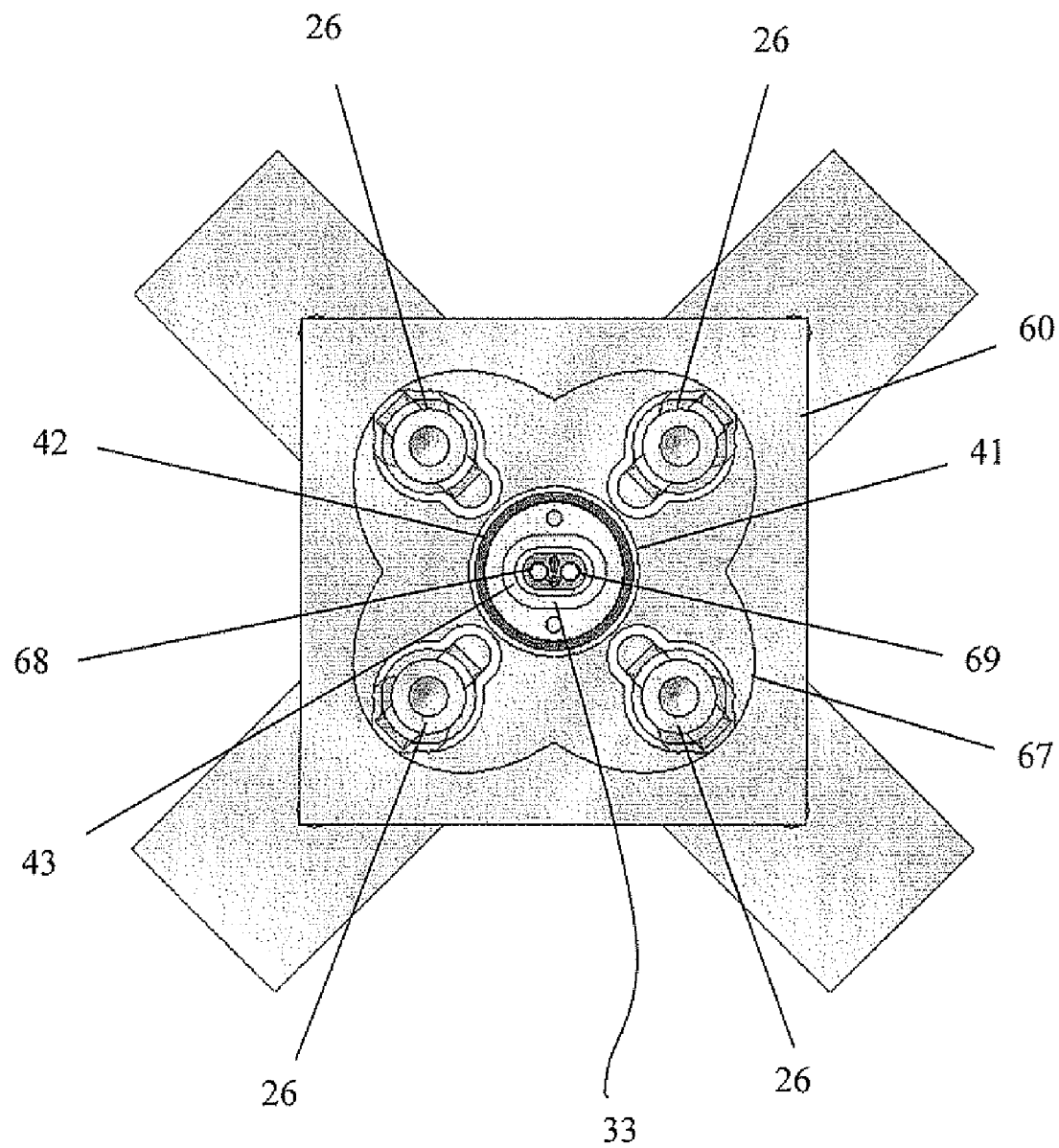
FIG. 4 shows a horizontal cross-sectional view through the infrared furnace and measuring assemblies depicted in FIG. 3.

In embodiments of the present invention, cavity 67 comprises a plurality of partial quadric cylindrical surfaces, where each partial quadric cylindrical surface is adjacent to one or more similar surfaces, as depicted generally in FIG. 4. The term "partial quadric cylindrical surface," as used herein, refers to a three dimensional surface that defines a partial cylinder whose cross sectional shape is that of a portion of a quadric curve, such as an ellipse. Thus, cavity 67 is defined by a series of four partial quadric cylinders that are each adjacent to two other partial quadric cylinders disposed on opposite sides of the cylinder in question.

In accordance with embodiments of the present invention, each partial quadric cylinder, can be either a partial elliptical or partial parabolic cylinder, which has a focus (which corresponds to a point in a plane of the partial quadric cylinder as viewed in cross-section, such as that depicted in FIG. 4) that corresponds to a position of a lamp 26.

FIG. 4 shows a horizontal cross-sectional view through the infrared furnace and measuring assemblies. In one embodiment of the present invention, cavity 67 of reflector body 60 comprises four intersecting elliptical cylinders arranged such that one focus of each elliptical cylinder is located equally spaced on a circle centered on the measuring assembly 41. A lamp 26 is located at each of the equally spaced foci. The second focus of each ellipse is collinear with each other second focus and the centerline of the measuring assembly 41. Sensor 43 is located symmetrically with respect to the centerline of the measuring assembly within cavity 33 of the enclosure 42 having a sample position 68 and a reference position 69. Referring again to FIG. 3, the cavity 67 of the reflector block 60 is designed to be approximately the same length (the ratio of length of reflector block cavity 67 and enclosure 42 is about 0.8 to 1.2, preferably about 0.9 to 1.1) as and aligned with conductive enclosure 42, such that enclosure 42 is surrounded by the reflector block cavity 67 over its entire length. In order to heat enclosure 42 efficiently, reflector block cavity 67 is designed not to extend substantially beyond the length of enclosure 42.

FIGS. 5-8 below depict aspects of the present invention in which the components are configured to provide a continuous supply of cryogenic liquid to a heat exchanger when a pump is submerged within an unpressurized liquid. The terms "unpressurized liquid" or "liquid in an unpressurized state" refer to the fact that an excess pressure is not exerted upon a cryogenic liquid, for example, when the liquid is in a storage dewar, so that the pressure above the cryogenic liquid is similar to that of the atmosphere outside the dewar. Accordingly, as described in detail below, a bellows pump of the present invention is configured to operate to pump cryogenic liquid in a dewar that contains one or more vent portals communicating with the ambient atmosphere outside the dewar, such that at least one portal can remain open to the atmosphere to allow excess vapor to vent to the outside atmosphere during operation of the pump. The pressure in the dewar is therefore maintained at a level approximately that of the outside atmosphere.

Thus, unlike positive pressurized cryogenic cooling systems, no excess pressure above the cryogenic liquid is needed for the positive displacement pump of the present invention to operate so that vent portals need not remain sealed. This facilitates replenishing the dewar with cryogenic liquid without interrupting operation of the pump, since the pump can remain operational while submerged while refilling of liquid can take place through a connection to a source of liquid nitrogen, typically a bulk storage dewar.

Figure 5:
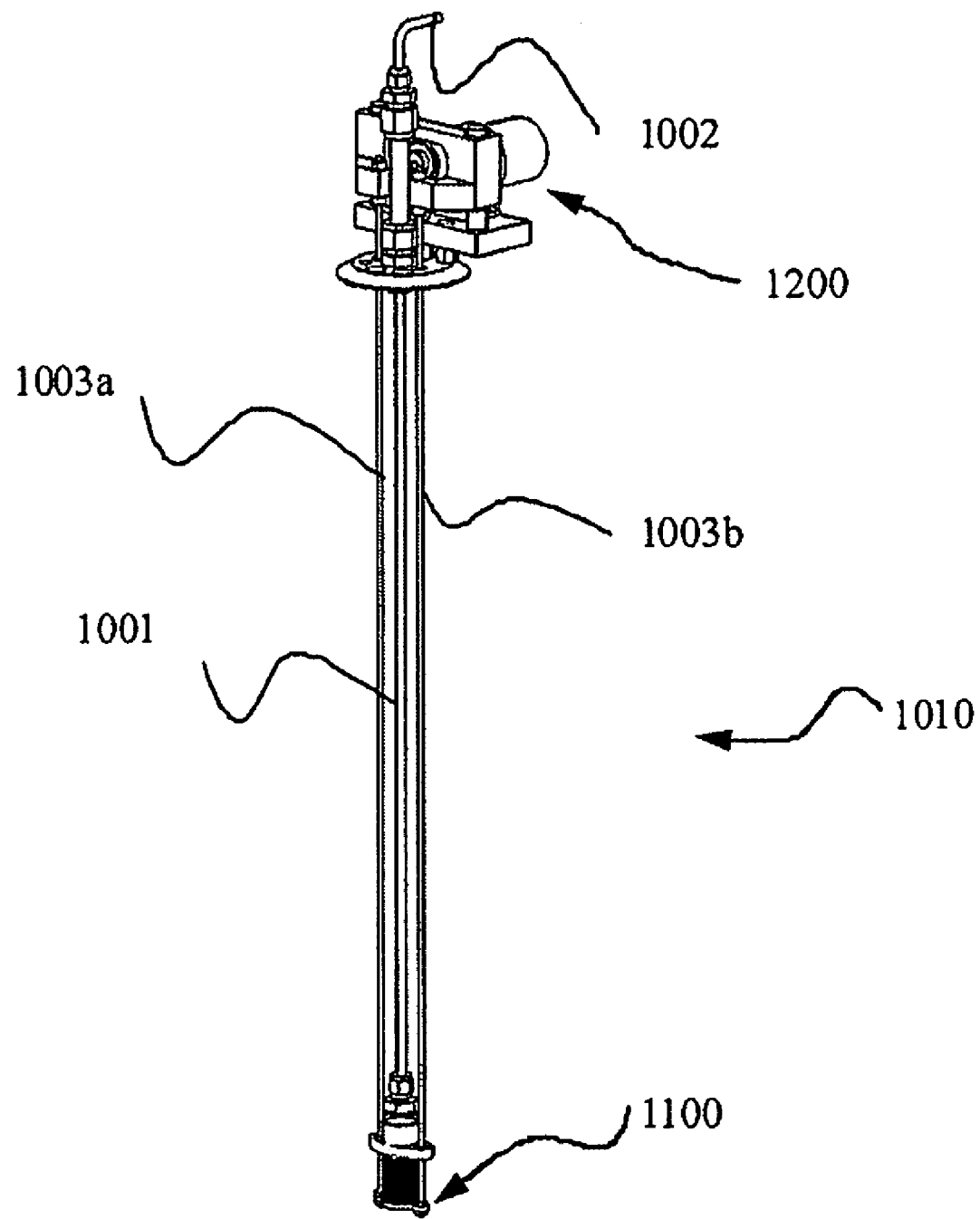
FIG. 5 shows an axonometric view of a liquid nitrogen pump assembly including a bellows pump assembly, drive assembly, drive rods and discharge tube, in accordance with an embodiment of the present invention.

In accordance with an embodiment of the present invention, FIG. 5 shows an overall view of a liquid nitrogen pump assembly comprising bellows pump assembly 1100, drive assembly 1200, discharge tube 1001 and drive rods 1003a and 1003b. Bellows pump assembly 1100 is connected to drive assembly 1200 by discharge tube 1001 through which liquid nitrogen can flow. Discharge tube 1001 has an end 1002 that is connected to a transfer line (not shown) that conducts liquid nitrogen to the apparatus to be cooled. Drive assembly 1200 supports bellows pump assembly 1100 via discharge tube 1001, which is made of a rigid material and serves to maintain a fixed separation between drive assembly 1200 and the top of pump assembly 1100. Drive rods 1003a and 1003b connect bellows pump assembly 1100 to drive assembly 1200 and impart the reciprocating motion of the drive assembly to the pump assembly.

Figure 6:
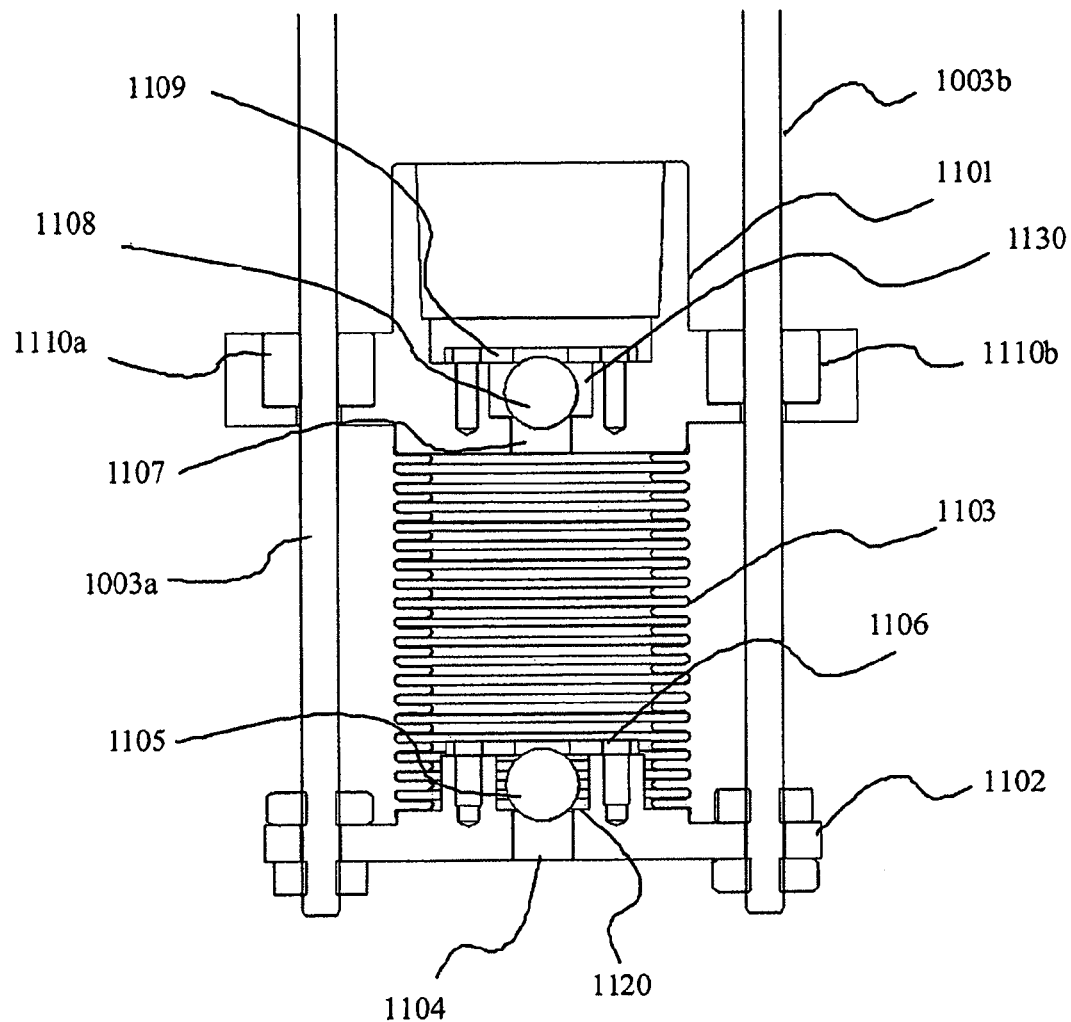
FIG. 6 shows a side view cross section of the bellows pump depicted in FIG. 6, in accordance with an embodiment of the present invention.

FIG. 6 is a vertical cross sectional view through bellows pump assembly 1100, showing details of its construction. The pump assembly comprises outlet head 1101, which contains a discharge port 1130, preferably configured as a discharge check valve assembly; inlet head 1102, which contains an inlet port 1120 that is preferably configured as a suction check valve assembly; and bellows 1103. Outlet head 1101 is connected to bellows 1103, which, in turn, is connected to inlet head 1102. The connections between the bellows and outlet and inlet heads are made using a liquid tight method that prevents liquid from leaking. In an exemplary embodiment of the invention, the inlet and outlet heads are made from stainless steel, the bellows is made from electrodeposited nickel, and the bellows and inlet and outlet heads are joined together by soldering. However, in other embodiments of the present invention, the inlet and outlet heads, as well as the bellows can be made from other materials that do not become brittle at cryogenic temperatures and may be joined using methods other than soldering.

Outlet head 1101 is connected in a liquid tight manner to discharge tube 1001 (not shown in FIG. 6), which is configured to support the pump assembly 1100 (see FIG. 5) and hold it motionless during operation of the pump. Inlet head 1102 is connected to drive rods 1003*a* and 1003*b*, which move parallel to the axis of the pump and impart the reciprocating motion of the drive assembly to the inlet head, thereby alternately compressing and extending the bellows and causing the volume enclosed by the outlet and inlet heads and the bellows to alternately decrease and increase. As noted above, inlet head 1102 preferably includes a suction check valve 1120, which comprises inlet port 1104, check ball 1105, and check ball retainer 1106. The discharge port 1130 is preferably a discharge check valve assembly that comprises discharge port 1107, check ball 1108, and check ball retainer 1109.

As depicted in FIG. 6, bellows 1103 extends and compresses along a vertical axis. FIG. 6 depicts a position of the pump in which both check valves are closed, which occurs both at the point of maximum compression or maximum extension of the bellows 1103. Extension of the bellows causes liquid in the dewar (not shown) to enter the pump through suction port 1104, displacing check ball 1105 against the force of gravity; check ball retainer 1106 limits check ball motion so that during the compression stroke the check ball closes the suction port under the action of gravity and the tendency of liquid to flow backward through the suction port, thereby preventing liquid from flowing back out of the pump through suction port 1104. In a preferred embodiment of the present invention, suction check valve 1120 is configured as a very low pressure drop ball check valve. This denotes that very little pressure drop is required to cause the valve to open to permit cryogenic liquid to flow through it. By thus configuring the suction check valve 1120 to open with low pressure drop, the pressure drop on the cryogenic liquid is minimal during each pump cycle when liquid is drawn into the bellows.

The low pressure drop configuration using a ball check valve promotes improved operation of the pump within the cryogenic liquid because the tendency to form vapor in the liquid entering or leaving the pump is minimized, Cryogenic liquid in an unpressurized dewar has a temperature close to the boiling point of the liquid. Accordingly, slight increases in temperature inside the dewar tend to markedly increase vaporization. Similarly, significant pressure drops induced above the cryogenic liquid, such as those caused by a large pressure drop check valve, would induce a large increase in the rate of vaporization of the cryogenic liquid passing through the check valve. Thus, in accordance with the present invention, a low pressure drop check valve reduces the amount of vapor evolved during each cycle of the pump by minimizing the pressure drop experienced by the liquid flowing through the check valves.

Compression of the bellows forces liquid contained within the pump to leave the pump through discharge port 1107, displacing check ball 1108 against the force of gravity; check ball retainer 1109 limits check ball motion so that during the extension stroke check ball 1108 closes the discharge port 1107 under the action of gravity and the tendency of liquid to flow backward through the discharge port, thereby preventing liquid from flowing back into the pump. Drive rods 1003*a* and 1003*b* pass through guide bushings 1110*a* and 1110*b* that are installed in the outlet head. The bushings allow free motion of the drive rods but constrain them to move parallel to the axis of the bellows, thereby stabilizing the bellows.

Figure 7:
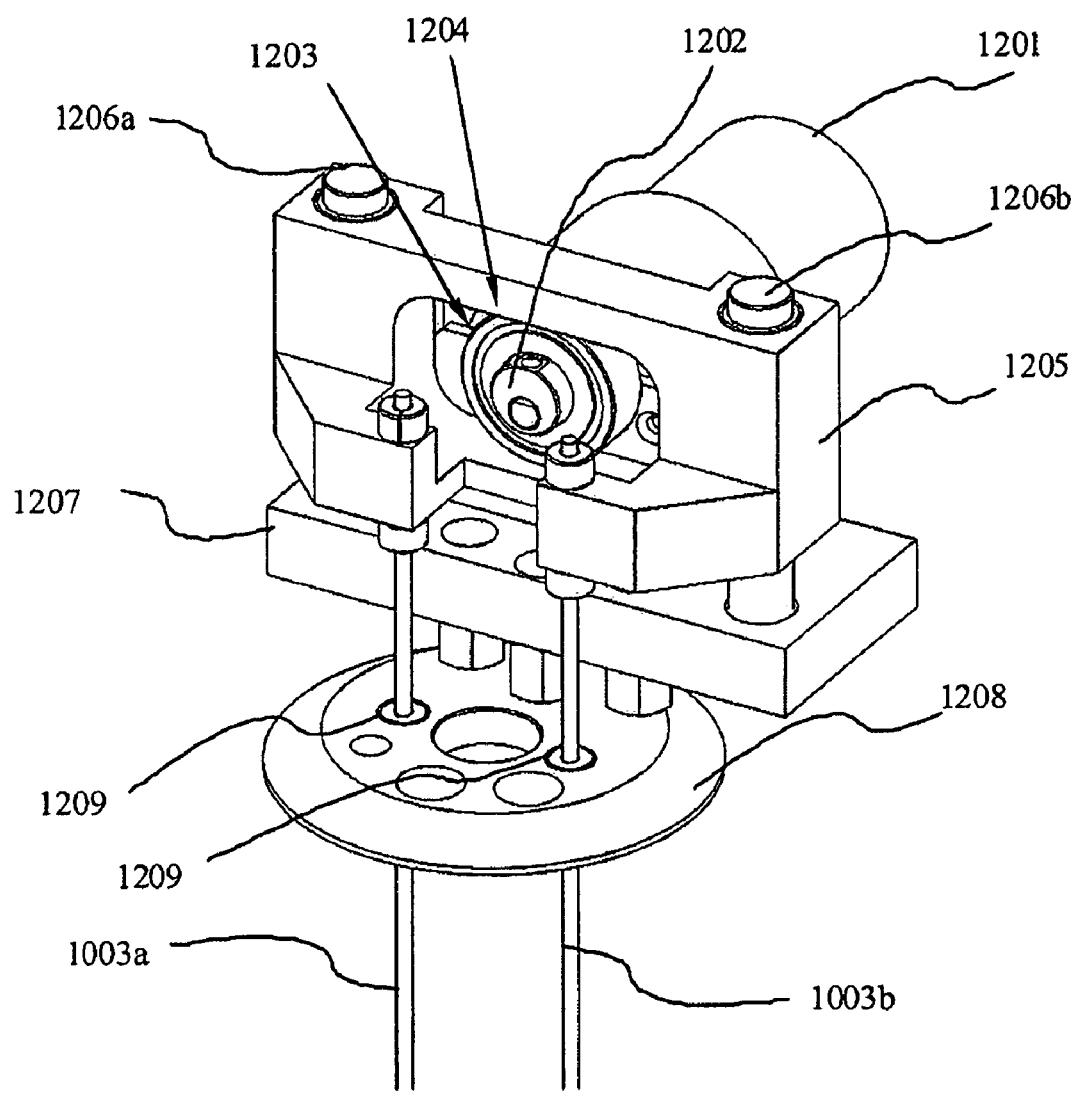
FIG. 7 shows an axonometric view of the drive assembly depicted in FIG. 6, according to an embodiment of the present invention.

FIG. 7 shows an axonometric view of drive assembly 1200. Gearmotor 1201 has an eccentric 1202 mounted on its output shaft; a ball bearing 1203 is mounted on the eccentric. The outer race of the ball bearing engages a slot 1204 in crosshead 1205 which is guided by a pair of shafts, 1206*a* and 1206*b* that constrain the crosshead to move parallel to the axes of the shafts, which are parallel to the axes of the pump and the drive rods. Shafts 206 and gearmotor 1201 are mounted on plate 1207. When the motor is energized, ball bearing 1203 rotates eccentrically on the gear motor output shaft, creating a reciprocating motion of the crosshead in a direction parallel to shafts 1206. Crosshead 1205 is fixedly attached to drive rods 1003*a* and 1003*b*, so that reciprocating motion of the crosshead imparts a reciprocating motion to the drive rods 1003*a* and 1003*b* and thereby to the pump. Mounting plate 1207 is attached to cover 1208, which is configured to clamp to the neck of a dewar containing the liquid. Drive rods 1003*a* and 1003*b* are configured to pass through cover 1208 and move freely in an up-and-down motion with respect to cover 1208. In one embodiment of the present invention, bushings 1209 installed in plate 1208 comprise a graphite material that facilitates smooth reciprocal motion of the drive rods 1003*a*, 1003*b* through cover 1208 over many pump cycles.

Thus, during operation of pump assembly 10, drive system 1200 is located external to the dewar, while bellows pump assembly 1100 is immersed in the liquid in the dewar and is driven by system 1200 via rods 1003*a* and 1003*b*, which are free to move with respect to cover 1208.

In accordance with the present invention, the overall distance between plate 1208 and bellows pump assembly 1100 is tailored according to the size of the dewar to be used. In one embodiment of the present invention, separate liquid nitrogen pump assemblies 1010 can be provided, wherein in each assembly 1010, the lengths of drive rods 1003*a*, 1003*b* and discharge tube 1001 are configured to locate bellows pump assembly 1100 near the bottom of a dewar into which the bellows pump is to be immersed when cover 1208 is clamped to the top of the dewar. Accordingly, the lengths of drive rods 1003*a*, 1003*b* and discharge tube 1001 could be for example one foot for use with a small dewar, or could be several feet for use with a larger dewar, or any other suitable length.

Figure 8:
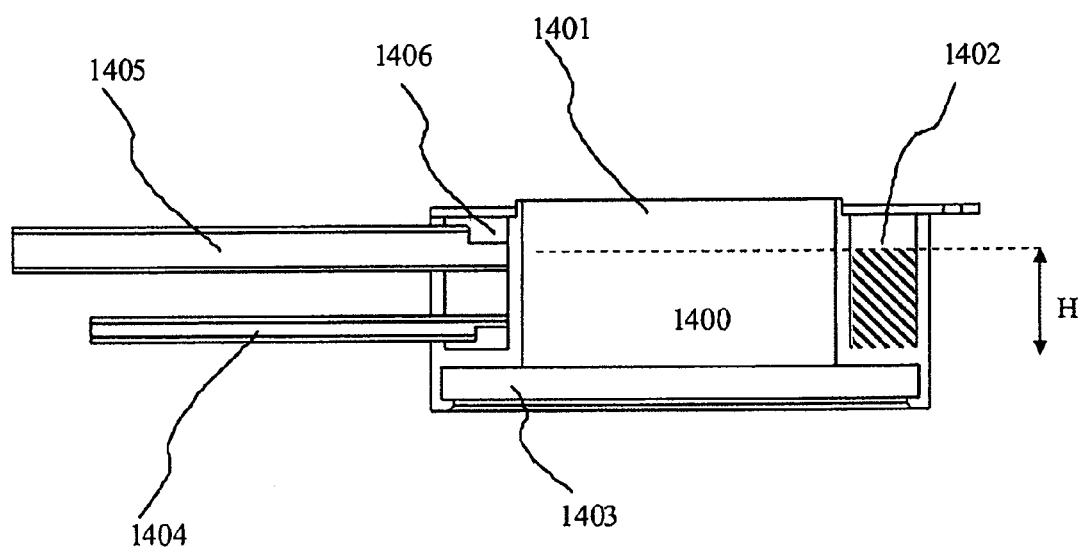
FIG. 8 shows a cross-section of a heat exchanger for a thermal analysis instrument that may be employed with the pump assembly of FIG. 6, according to another embodiment of the present invention.

FIG. 8 shows a cross sectional view through a heat exchanger 1400 that may be used to cool a thermal analysis or other instrument, in accordance with an exemplary embodiment of the present invention. The body 1401 of the heat exchanger is preferably in the form of a ring made of high thermal conductivity material, and contains an annular cavity 1402 to receive the coolant. The walls and the floor of the cavity comprise the heat exchange surface. In the exemplary embodiment shown, body 1401 comprises two parts (not shown), a first portion that includes the walls and floor of the annular cavity and a cover plate that is soldered to the first portion and which forms the top of the annular cavity. Heat exchanger 1400 incorporates a mounting surface 1403, by which it may be coupled to a thermal analysis apparatus, for example, to a sample stage of the apparatus. Liquid is supplied to the annular cavity 1402 by an inlet tube 1404 that discharges liquid into the annular cavity. Inlet tube 1404 is connected to end 1002 of the discharge tube of the pump by a suitable conduit (not shown). Preferably, vapor and excess liquid is discharged from the heat exchanger by exhaust tube 1405 that is connected to the dewar by a suitable conduit (not shown) to return the mixture of liquid and vapor to the dewar. The discharge tube is constructed with a weir 1406, over which liquid leaving the heat exchanger must flow, thereby regulating the level of liquid in the heat exchanger to be about the same height H or slightly higher than the top of the weir.

In the embodiment illustrated in FIG. 8, heat exchanger 1400 is in the form of a ring to accommodate a device coupled to heat exchanger 1400, such as the device disclosed in U.S. Pat. No. 6,523,998 to Danley, et. al. In accordance with embodiments of the present invention, the exact structure of the heat exchanger is tailored according to the thermal interface of the instrument to which it is coupled. Features common to any such heat exchanger include a cavity to contain the liquid having wetted heat exchange surfaces that are sufficiently large that adequate heat can be exchanged, a mounting surface to attach the heat exchanger to the instrument, and inlet and outlet connections to the heat exchanger. In other embodiments of the present invention, the heat exchanger can be an integral part of the instrument to be cooled, such that it is inseparable with the instrument.

In accordance with a preferred embodiment of the present invention, a pump system and heat exchanger, such as those described with respect to FIGS. 1-4 above, are configured to supply a continuous flow of cryogenic liquid to the heat exchanger that is sufficient to compensate for a maximum heat load applied to the heat exchanger. This denotes the fact that the continuous flow of cryogenic liquid is sufficient to remove heat from the heat exchanger by boiling heat transfer at a rate that is sufficient to prevent the critical heat flux point from being reached even under maximum heat load.

Advantageously, with the use of a positive displacement pump having low pressure drop suction and discharge check valves immersed in an unpressurized dewar, continuous flow of liquid can be supplied to a heat exchanger for any desired length of time, since the dewar can be refilled without stopping the pump. In accordance with embodiments of the present invention, in order to assure that the continuous cryogenic liquid flow is sufficient to prevent the critical heat flux point from being reached, the overall size and shape of the heat exchanger can be tailored according to the expected or measured heat load applied to a sample stage. For example, a heat exchanger can be configured such that the critical heat flux point is not reached so long as the exchanger remains full of liquid (say, up to the weir height). During an experiment, the positive displacement pump need thereby only operate to provide sufficient flow rate such that some liquid is continuously returned to the dewar, thus ensuring that liquid remains in the heat exchange cavity up to the height of the weir. This requires no active control system that may be complicated to operate, and allows for variations in flow rate, so long as the flow rate is sufficient to maintain some liquid return to the dewar at all times.

Thus, although the flow rate of cryogenic liquid through the heat exchanger may vary as the bellows pump cycles from an expanded state to a compressed state, in accordance with embodiments of the present invention, the stroke (back and forth distance traveled by the bellows) and diameter of the bellows, the diameter and length of lines conducting the cryogenic liquid, and the depth of the heat exchange cavity containing the liquid, among other factors, can be tailored to ensure that the heat exchange cavity remains full of liquid, such that liquid is returned to the dewar at all points of the pump cycle and under all heat flux conditions anticipated for the sample stage.

In accordance with an embodiment of the present invention, pump system 10 is also fitted with a system (not shown) to detect the level of liquid nitrogen in the storage dewar. One embodiment of the present invention comprises a liquid level detection system that contains a pair of self-heated thermal switches that close when immersed in liquid nitrogen and open when surrounded by vapor. One of the switches is mounted in the dewar at an elevation corresponding to the full level of liquid and closes to indicate that the dewar is full. The other switch is located at an elevation corresponding to the level at which the dewar should be refilled and opens to indicate that it should be refilled. The switches may simply provide a level indication for example by illuminating indicating lamps or may be used to operate a valve by which liquid may be automatically added to the dewar to refill it. Alternatively, a continuous level measuring system, such as a capacitive level detection (see Guy K. White, "Experimental Techniques in Low-Temperature Physics" 3ed, 1979, Oxford Science Publications, pp 50-54) system may be used. The capacitive level detection system may simply provide level indication via a meter or other suitable indicating device. Alternatively, the detection system may be used to supply a level indication to a logical circuit that actuates a valve by which liquid may be automatically added to the dewar when the liquid level falls to a preset value.

In summary, in accordance with embodiments of the present invention, a heat flux DSC is configured to provide more rapid sample heating and cooling rates in comparison to conventional systems. Additionally, configurations of the present invention provide a more efficient arrangement for heating a DSC when the heat source is a plurality of lamps emitting infrared radiation. Finally, more versatile sample measurements are provided by embodiments in which a heat flux DSC includes a configurable thermal resistor. Thus, the thermal conductivity of the thermal resistor can be decreased during sample heating and increased during sample cooling, which allows the sample heating rate and sample cooling rate to be independently maximized during a single experiment.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure.

Notably, the scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A differential scanning calorimeter comprising:
    a high thermal conductivity enclosure having a high emissivity outer surface;
    a sensor assembly disposed within the high thermal conductivity enclosure;
    an infrared lamp assembly disposed circumferentially around the high thermal conductivity enclosure and including a cavity having a length approximately the same as that of the high thermal conductivity enclosure;
    a thermal resistor coupled to the high thermal conductivity enclosure and disposed substantially outside a region defined by the cavity of the infrared lamp assembly; and a heat sink thermally coupled to the thermal resistor and to the infrared lamp assembly, wherein the thermal resistor comprises one of a plurality of rods or a gas-filled gap.

2. The differential scanning calorimeter of claim 1, wherein the high thermal conductivity enclosure comprises silver.

3. The differential scanning calorimeter of claim 1, wherein the high emissivity outer surface comprises an electroplated layer.

4. The differential scanning calorimeter of claim 1, wherein the infrared lamp assembly comprises a polished surface having a coating that has an infrared reflectivity of greater than about 0.9 for infrared wavelengths up to about 12 micrometers wavelength.

5. The differential scanning calorimeter of claim 1,
wherein the infrared lamp assembly comprises a plurality of tubular lamps arranged with a longitudinal axis parallel to an axis of the high thermal conductivity enclosure and an infrared reflector comprising a plurality of partial quadric cylindrical surfaces that each describe a portion of a cylindrical shape having a focus collinear with a position of a tubular lamp.

6. The differential scanning calorimeter of claim 5, wherein each partial quadric cylindrical shape corresponds to an elliptical cylindrical shape, wherein a position of each tubular lamp corresponds to a first focus of each elliptical cylindrical shape, and wherein a second focus of each cylindrical shape is collinear with a second focus of each other elliptical cylindrical shape.

7. A differential scanning calorimeter comprising:
a high thermal conductivity enclosure having a high emissivity outer surface;
a sensor assembly disposed within the high thermal conductivity enclosure;
an infrared lamp assembly disposed circumferentially around the high thermal conductivity enclosure and including a cavity having a length approximately the same as that of the high thermal conductivity enclosure;
a thermal resistor coupled to the high thermal conductivity enclosure and disposed substantially outside a region defined by the cavity of the infrared lamp assembly; and
a heat sink thermally coupled to the thermal resistor and to the infrared lamp assembly,
wherein the sensor assembly comprises a sample holder and reference holder.

8. The differential scanning calorimeter of claim 7, wherein the sample holder and the reference holder each comprise a cavity for receiving a respective sample container and a respective reference container.

9. A differential scanning calorimeter comprising:
a high thermal conductivity enclosure having a high emissivity outer surface;
an infrared lamp assembly disposed circumferentially around the high thermal conductivity enclosure and including a cavity having a length approximately the same as that of the high thermal conductivity enclosure, the infrared lamp assembly comprising a plurality of tubular lamps arranged with a longitudinal axis parallel to an axis of the high thermal conductivity enclosure and an infrared reflector comprising a plurality of portions of elliptical cylindrical surfaces that each describe a cylindrical shape having a focus collinear with a position of a tubular lamp; and
a thermal resistor thermally coupled to the high thermal conductivity enclosure,
wherein the thermal resistor comprises one of a plurality of rods or a gas-filled gap.

10. The differential scanning calorimeter of claim 9, further comprising a heat sink thermally coupled to the thermal resistor and to the infrared reflector.

11. The differential scanning calorimeter of claim 9, wherein the lamp assembly comprises a plurality of T-3 configuration lamps.

12. The differential scanning calorimeter of claim 9, wherein the high thermal conductivity enclosure comprises cylinder walls having a high thermal conductivity inner portion and a high emissivity outer coating.

13. The differential scanning calorimeter of claim 9, wherein the high thermal conductivity material comprises silver.

14. The differential scanning calorimeter of claim 9, wherein the high emissivity outer surface comprises an electroplated layer.

15. A differential scanning calorimeter, comprising:
a high thermal conductivity enclosure having a high emissivity outer surface;
an infrared lamp assembly disposed circumferentially around the high thermal conductivity enclosure and including a cavity having a length approximately the same as that of the high thermal conductivity enclosure, the infrared lamp assembly comprising a plurality of tubular lamps arranged with a longitudinal axis parallel to an axis of the high thermal conductivity enclosure and an infrared reflector comprising a plurality of partial cylindrical surfaces that each describe a cylindrical shape having a first focus collinear with a position of a tubular lamp and a second focus collinear with an axis of the high thermal conductivity enclosure;
a thermal resistor coupled to the high thermal conductivity enclosure; and
a heat sink thermally coupled to the thermal resistor; and
a sensor assembly comprising a sample holder and a reference holder configured to receive and hold a respective sample container and a respective reference container;
wherein the thermal resistor is operable to vary the thermal resistance between the high thermal conductivity enclosure and the heat sink during sample measurement; and
wherein the thermal resistor is disposed substantially outside the cavity of the infrared lamp assembly.

16. The differential scanning calorimeter of claim 15, wherein the thermal resistor comprises a thin-walled cylinder.

17. The differential scanning calorimeter of claim 15, wherein the sample holder and the reference holder each comprise a cavity for receiving a respective sample container and a respective reference container.

18. The differential scanning calorimeter of claim 15, wherein the thermal resistor comprises a gas-filled gap.

19. The differential scanning calorimeter of claim 18, wherein the thermal resistor comprises a high thermal conductivity layer integral with the high thermal conductivity enclosure and disposed at a flat end of the high thermal conductivity enclosure.

20. The differential scanning calorimeter of claim 18, wherein the thermal resistor is configured to receive and retain gas from a gas supply.

21. A differential scanning calorimeter for efficient heating during rapid thermal heating, comprising:
a high thermal conductivity enclosure having a high emissivity outer surface;
a sensor assembly disposed within the high thermal conductivity enclosure;

an infrared lamp assembly disposed circumferentially around the high thermal conductivity enclosure and including a cavity having a length approximately the same as that of the high thermal conductivity enclosure, wherein the infrared lamp assembly comprises a plurality of tubular lamps arranged with a longitudinal axis parallel to an axis of the high thermal conductivity enclosure and wherein, each of the infrared lamps arranged within a cavity is surrounded by an infrared reflector;

a thermal resistor coupled to the high thermal conductivity enclosure, wherein the thermal resistor is disposed substantially outside the cavity of the infrared lamp assembly; and a heat sink thermally coupled to the thermal resistor and to the infrared reflector, wherein the thermal resistor is coupled to a flat end of the high thermal conductivity enclosure and comprises one of a plurality of rods or a gas-filled gap.

22. The differential scanning calorimeter of claim 21, wherein the high thermal conductivity enclosure comprises silver.

23. The differential scanning calorimeter of claim 21, wherein the high emissivity outer surface comprises an electroplated layer.

24. The differential scanning calorimeter of claim 21, wherein the heat sink is disposed circumferentially around the infrared lamp assembly.

25. The differential scanning calorimeter of claim 21, wherein the infrared reflector comprises a plurality of portions of quadric cylindrical surfaces that each describe a portion of a cylindrical shape having a first focus collinear with a position of a tubular lamp.

26. The differential scanning calorimeter of claim 25, wherein the portions of quadric cylindrical surfaces comprise portions of elliptical cylinders, wherein a second focus of each elliptical cylinder is collinear with an axis of the high thermal conductivity enclosure, and wherein the infrared reflector comprises a polished surface having a coating that has an infrared reflectivity of greater than about 0.9 for infrared wavelengths up to about 12 micrometers wavelength.

27. A differential scanning calorimeter comprising:
a high thermal conductivity enclosure having a high emissivity outer surface;
a sensor assembly disposed within the high thermal conductivity enclosure;
an infrared lamp assembly disposed circumferentially around the high thermal conductivity enclosure and including a cavity having a length substantially similar to that of the high thermal conductivity enclosure; and
a thermal resistor coupled to the high thermal conductivity enclosure,
wherein the thermal resistor is disposed substantially outside the cavity of the infrared lamp assembly, and
wherein the thermal resistor comprises a plurality of rods.

28. The differential scanning calorimeter of claim 27, wherein the high emissivity outer surface comprises an electroplated layer.

29. The differential scanning calorimeter of claim 27, wherein the high thermal conductivity enclosure comprises silver.

30. The differential scanning calorimeter of claim 27, further comprising a heat sink that is thermally coupled to the thermal resistor.

31. The differential scanning calorimeter of claim 30, wherein the heat sink is disposed circumferentially around the infrared lamp assembly.

32. The differential scanning calorimeter of claim 31, wherein the heat sink comprises a set of cooling fins.

33. The differential scanning calorimeter of claim 31, wherein the heat sink comprises a cavity configured to contain flowing liquid.

34. The differential scanning calorimeter of claim 33, wherein the flowing liquid comprises liquid nitrogen.

35. A method of performing differential scanning calorimetry, comprising:
receiving a sample in a sensor assembly disposed within a high thermal conductivity enclosure having a high emissivity outer surface;
heating the sample using an infrared lamp assembly disposed circumferentially around the high thermal conductivity enclosure and including a cavity having a length approximately the same as that of the high thermal conductivity enclosure;
providing a thermal resistor coupled to the high thermal conductivity enclosure, wherein the thermal resistor is disposed substantially outside the cavity of the infrared lamp assembly; and
dissipating heat from the sample using a heat sink thermally coupled to the thermal resistor and to the infrared lamp assembly,
wherein the thermal resistor comprises one of a plurality of rods or a gas-filled gap.

36. The method of claim 35, wherein the high thermal conductivity enclosure comprises silver.

37. The method of claim 35, wherein the high emissivity outer surface comprises an electroplated layer.

38. The method of claim 35,
wherein the infrared lamp assembly comprises a plurality of tubular lamps arranged with a longitudinal axis parallel to an axis of the high thermal conductivity enclosure and an infrared reflector comprising a plurality of portions of quadric cylindrical surfaces that each describe a portion of a quadric cylindrical shape having a focus collinear with a position of a tubular lamp.

39. The method of claim 38, wherein each portion of a quadric cylindrical shape corresponds to an elliptical cylindrical shape, wherein a position of each tubular lamp corresponds to a first focus of each elliptical cylindrical shape, and wherein a second focus of each cylindrical shape is collinear with a second focus of each other elliptical cylindrical shape.

40. A method of performing differential scanning calorimetry, comprising:
receiving a sample in a sensor assembly disposed within a high thermal conductivity enclosure having a high emissivity outer surface;
heating the sample using an infrared lamp assembly disposed circumferentially around the high thermal conductivity enclosure and including a cavity having a length approximately the same as that of the high thermal conductivity enclosure;
providing a thermal resistor coupled to the high thermal conductivity enclosure, wherein the thermal resistor is disposed substantially outside the cavity of the infrared lamp assembly; and
dissipating heat from the sample using a heat sink thermally coupled to the thermal resistor and to the infrared lamp assembly,
wherein the sensor assembly comprises a sample holder and reference holder.

41. The method of claim 40, wherein the sample holder and the reference holder each comprise a cavity for receiving a respective sample container and a respective reference container.

42. A differential scanning calorimeter comprising:
a high thermal conductivity enclosure having a high emissivity outer surface;
an infrared lamp assembly disposed circumferentially around the high thermal conductivity enclosure and including a cavity having a length approximately the same as that of the high thermal conductivity enclosure, the infrared lamp assembly comprising a plurality of tubular lamps arranged with a longitudinal axis parallel to an axis of the high thermal conductivity enclosure and an infrared reflector comprising a plurality of portions of elliptical cylindrical surfaces that each describe a cylindrical shape having a focus collinear with a position of a tubular lamp;
a thermal resistor thermally coupled to the high thermal conductivity enclosure; and
a sensor assembly disposed within the high thermal conductivity enclosure, the sensor assembly comprising a sample holder and reference holder.

43. The differential scanning calorimeter of claim 42, wherein the sample holder and the reference holder each comprise a cavity for receiving a respective sample container and a respective reference container.

* * * * *